United States Patent [19]
Buchecker et al.

[11] Patent Number: 5,447,658
[45] Date of Patent: Sep. 5, 1995

[54] TRICYCLIC FLUOROBENZONITRILE DERIVATIVES

[75] Inventors: Richard Buchecker, Zurich; Teodor Lukàc, Aesch; Martin Schadt, Seltisberg, all of Switzerland; Haruyoshi Takatsu, Kodaira, Japan; Alois Villiger, Basle, Switzerland

[73] Assignees: Hoffman-La Roche Inc., Nutley, N.J.; Dainipppon Ink and Chemicals, Inc., Tokyo, Japan

[21] Appl. No.: 261,625

[22] Filed: Jun. 17, 1994

Related U.S. Application Data

[63] Continuation of Ser. No. 50,476, May 18, 1993, abandoned.

[30] Foreign Application Priority Data

Oct. 1, 1991 [CH] Switzerland ............... 2899/91
Jul. 23, 1992 [CH] Switzerland ............... CHX

[51] Int. Cl.$^6$ .......................... C07D 319/06
[52] U.S. Cl. ..................... 252/299.6; 549/369
[58] Field of Search ............... 549/369; 252/299.61

[56] References Cited

U.S. PATENT DOCUMENTS

| | | | |
|---|---|---|---|
| 4,676,604 | 6/1987 | Petrzilka | 350/350 |
| 4,784,471 | 11/1988 | Wächtler et al. | 350/350 |
| 5,230,826 | 7/1993 | Boller | 252/299.61 |

FOREIGN PATENT DOCUMENTS

| | | |
|---|---|---|
| 433 836 | 6/1991 | European Pat. Off. |
| 3515633 | 11/1986 | Germany |
| 91/02780 | 3/1991 | WIPO |
| 91/09026 | 6/1991 | WIPO |
| 91/16321 | 10/1991 | WIPO |

OTHER PUBLICATIONS

Derwent Abstract 91-052386/08 (1991) for WO 91/02780.
Derwent Abstract 86-299052/46 (1986) for DE3515633.

*Primary Examiner*—C. Warren Ivy
*Assistant Examiner*—Raymond Covington
*Attorney, Agent, or Firm*—George M. Gould; George W. Johnston; Robert A. Silverman

[57] ABSTRACT

Compounds of the general formula

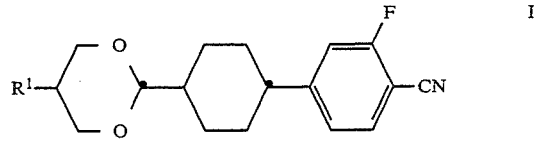

wherein $R^1$ represents vinyl or straight-chain alkenyl with 3 to 7 carbon atoms, the manufacture of such compounds, liquid crystalline mixtures which contain such compounds as well as the use of such compounds for electro-optical purposes.

7 Claims, No Drawings

TRICYCLIC FLUOROBENZONITRILE DERIVATIVES

This is a continuation of application Ser. No. 08/050,476 filed May 18, 1993, now abandoned.

The present invention is concerned with compounds having a fluorocyanophenyl head group, their manufacture, liquid crystalline mixtures which contain these compounds as well as their use for electro-optical purposes.

Liquid crystals are used primarily as dielectrics in indicating devices, since the optical properties of such substances can be influenced by an applied voltage. Electro-optical devices based on liquid crystals are well-known to a person skilled in the art and can be based on various effects. The most common indicating devices are based on the Schadt-Helfrich effect and have a twisted nematic structure. Examples of such cells are TN cells ("twisted nematic") and STN cells (supertwisted nematic).

The liquid crystal materials for such cells must have a good chemical and thermal stability and a good stability towards electric fields and electromagnetic radiation. Further, the liquid crystal materials should have low viscosity and in the cells should give short response times, low threshold potentials and a high contrast. They should have a suitable mesophase at usual operating temperatures, for example a nematic or cholesteric mesophase for the cells mentioned above. Further, the dielectric anisotropy should be as high as possible.

Since liquid crystals are usually used as mixtures of several components, it is also important that the components have a good miscibility with one another.

Such compounds are now made available in accordance with the present invention.

The present invention provides compounds of the general formula

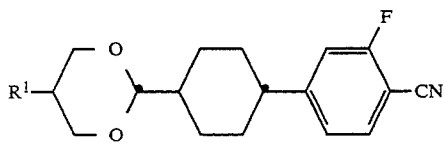

wherein $R^1$ represents vinyl or straight-chain alkenyl with 3 to 7 carbon atoms.

The compounds in accordance with the invention are liquid crystals having a broad nematic phase and a comparatively high clearing point. They have a surprisingly high dielectric anisotropy with relatively low rotation viscosity and lead to a low threshold potential and short response times.

The compounds in accordance with the invention are suitable for indicating devices having a twisted nematic structure, i.e. for TN cells and STN cells. By virtue of their good miscibility with one another and with known liquid crystal materials they can be used in comparatively high concentrations. They are especially suitable as components of nematic and cholesteric mixtures.

Examples of straight-chain alkenyl residues with 3 to 7 carbon atoms are 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4-hexenyl, 4-heptenyl, 5-hexenyl, 5-heptenyl, 6-heptenyl and the like. Preferred residues $R^1$ are vinyl and straight-chain alkenyl residues with 3 to 5 carbon atoms, especially vinyl, 1E-propenyl, 1E-butenyl, 1E-pentenyl, 3-butenyl and 3E-pentenyl.

The compounds of general formula I can e.g. be manufactured with the invention by reacting an enol ether of the formula

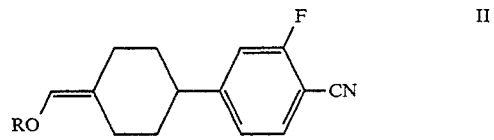

wherein R signifies lower alkyl, with a 1,3-diol of the formula

wherein $R^1$ has the above significance, in an inert organic solvent while heating in the presence of water and an acid catalyst.

The term "lower alkyl" embraces in this connection alkyl residues with 1 to 5 carbon atoms such as, for example, methyl, ethyl, propyl, butyl, pentyl and the like, especially methyl, ethyl and propyl.

As organic solvents in the scope of the present invention there come into consideration, for example, aromatic hydrocarbons such as toluene, xylene and the like or chlorinated hydrocarbons such as chloroform, dichloroethylene and the like. The heating is conveniently effected for a few minutes to a few degrees C below the reflux temperature of the solvent and then at the reflux temperature. As acid catalysts there come into consideration strong protonic acids such as, for example, $H_2SO_4$, p-toluenesulphonic acid, Amberlite 15® and the like.

The enol ether II is reacted in an appropriate manner, e.g. together with one equivalent or less than one equivalent of water, catalytic amounts of acid and a 1,3-diol of formula III, for example in toluene while distilling off alcohol and water. In this manner the aldehyde formed from the enol ether as an intermediate is acetalized directly and without isolation.

The compounds of formula I can be used in the form of mixtures with one another and/or with other liquid crystal components, such as e.g. with substances from the classes of Schiff's bases, azobenzenes, azoxybenzenes, phenyl benzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances will be known to a person skilled in the art and, moreover, many of them are commercially available.

The liquid crystalline mixtures in accordance with the invention contain at least two components of which at least one component is a compound of formula I. A second component and, optionally, additional components can be further compounds of formula I or other liquid crystal components. The compounds of formula I are especially suitable for nematic mixtures or, insofar as at least one component of the mixture is optically active, also for cholesteric mixtures.

Having regard to the good solubility of the compounds of formula I and having regard to their good miscibility with one another, they can be present in the mixtures in accordance with the invention in a relatively high amount. In general, however, a content of about 1–50 wt. %, especially about 3–20 wt. %, of compounds of formula I is preferred.

The mixtures in accordance with the invention preferably contain, in addition to one or more compounds of formula I, one or more compounds from the group of compounds of the general formulae

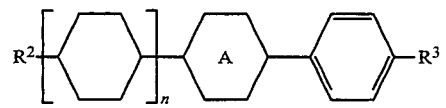

IV

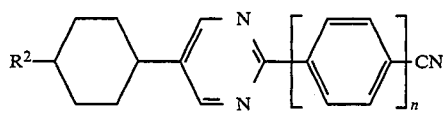

V

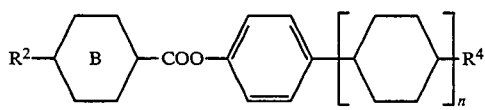

VI

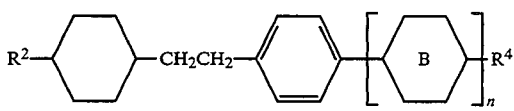

VII

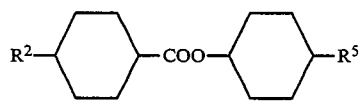

VIII

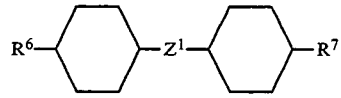

IX

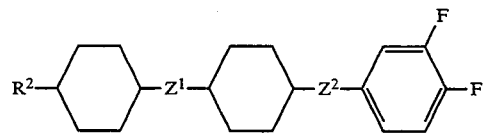

X

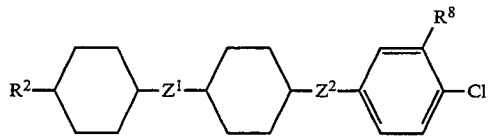

XI

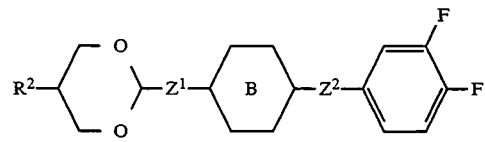

XII

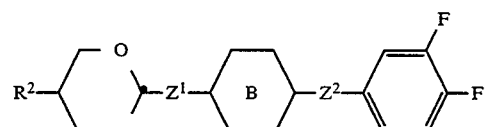

XIII

-continued

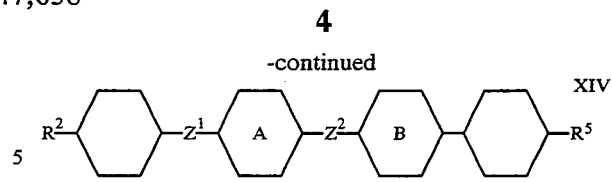

XIV

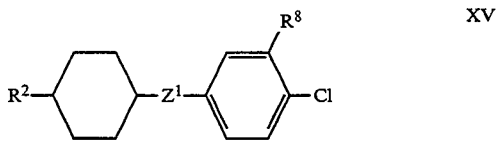

XV

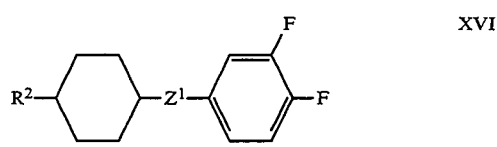

XVI

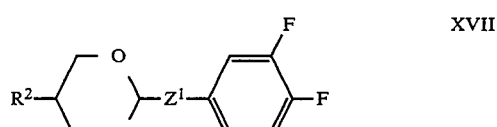

XVII

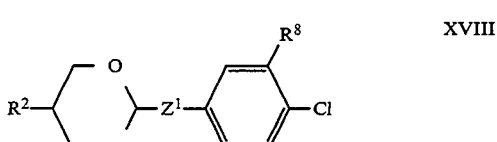

XVIII

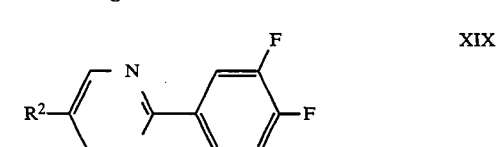

XIX

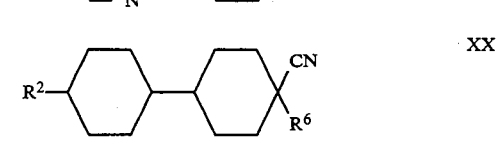

XX

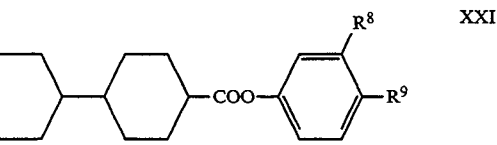

XXI

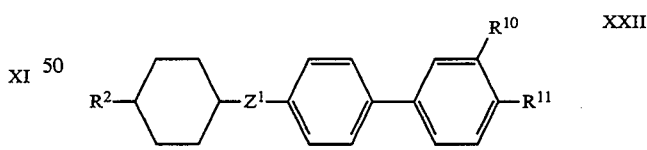

XXII wherein $R^2$, $R^5$ signify alkyl, alkoxyalkyl, 3E-alkenyl, 4-alkenyl or on saturated rings also 1E-alkenyl;

n signifies 0 or 1;

ring $A^1$ denotes 1,4-phenylene, pyridine-2,5-diyl, pyrimidine-2,5-diyl, trans-1,4-cyclohexylene or trans-1,3-dioxane-2,5-diyl;

$R^3$ represents cyano, isothiocyanato, fluorine, alkyl, 3E-alkenyl, 4-alkenyl, alkoxy, 2E-alkenyloxy, 3-alkenyl-oxy or 1-alkynyl;

ring B signifies 1,4-phenylene or trans-1,4-cyclohexylene;

$R^4$ denotes alkyl, 3E-alkenyl, 4-alkenyl or on trans-1,4-cyclohexylene also 1E-alkenyl or on 1,4-phenylene also cyano, isothiocyanato, alkoxy, 2E-alkenyloxy or 3-alkenyloxy;

$R^6$ signifies alkyl, 1E-alkenyl, 3E-alkenyl or 4-alkenyl;

$R^7$ represents cyano, alkyl, 1E-alkenyl, 3E-alkenyl, 4-alkenyl, alkoxy, 2E-alkenyloxy, 3-alkenyloxy, alkoxy-methyl or (2E-alkenyl)oxymethyl;

$Z^1$, $Z^2$ denote a single covalent bond or —CH$_2$CH$_2$—, with two aromatic rings always being linked by a single covalent bond;

$R^8$ signifies hydrogen, fluorine or chlorine;

$R^9$ represents cyano, fluorine or chlorine;

$R^{10}$ denotes hydrogen of fluorine;

$R^{11}$ represents fluorine or chlorine.

The above term "saturated ring" embraces trans-1,4-cyclohexylene and trans-1,3-dioxane-2,5-diyl. Residues $R^2$ to $R^7$ each preferably have 1 to 12 carbon atoms, particularly 1 to 7 carbon atoms. Straight-chain residues are generally preferred. The term "alkyl" signifies in this connection preferably straight-chain residues with 1 to 12 carbon atoms, preferably with 1 to 7 carbon atoms, such as, for example, methyl, ethyl, propyl, butyl, pentyl, hexyl or heptyl.

The term "alkyloxyalkyl" signifies in this connection preferably straight-chain residues such as, for example, methoxymethyl, ethoxymethyl, propyloxymethyl, butyloxymethyl and the like.

The term "alkyloxy" signifies in the connection preferably straight-chain residues such as, for example, methoxy, ethoxy, propyloxy, butyloxy, pentyloxy, hexyloxy, heptyloxy and the like.

The term "1E-alkenyl" signifies in the connection preferably straight-chain alkenyl residues in which the double bond is situated in the 1-position, such as, for example, vinyl, 1E-propenyl, 1E-butenyl, 1E-pentenyl, 1E-hexenyl, 1E-heptenyl and the like.

The term "3E-alkenyl" signifies in this connection preferably straight-chain alkenyl residues in which the double bond is situated in the 3-position, such as, for example, 3-butenyl, 3E-pentenyl, 3E-hexenyl, 3E-heptenyl and the like.

The term "4-alkenyl" signifies in this connection preferably straight-chain alkenyl residues in which the double bond is situated in the 4-position, such as, for example, 4-pentenyl, 4-hexenyl, 4-heptenyl and the like.

The term "2E- or 3Z-alkenyloxy" signifies in this connection preferably straight-chain alkenyloxy residues in which the double bond is situated in the 2- or 3-position and E or Z indicates the preferred configuration, such as, for example, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy and the like.

The term "1-alkynyl" signifies in the connection preferably straight-chain alkynyl residues in which the triple bond is situated in the 1-position, such as, for example, ethynyl, 1-propynyl, 1-butynyl, 1-pentynyl and the like.

The manufacture of the liquid crystalline mixtures and of the electro-optical devices can be effected in a manner known per se.

The invention is illustrated in more detail by the following Examples. In the Examples C signifies a crystalline phase, N signifies a nematic phase and I signifies the isotropic phase. $V_{10}$ denotes the voltage for 10% transmission $t_{on}$ and $t_{off}$ denote, respectively, the switching-on time and the switching-off time. $\Delta n$ denotes the optical anisotropy.

EXAMPLE 1

A mixture of 0.98 g of 2-fluoro-4-[4-(methoxymethylidene)cyclohexyl]benzonitrile (U.S. Pat. No. 4,784,471), 0.70 g of 2-(1E-pentenyl)-1,3-propanediol, 45 ml of toluene, 2 ml of water and 10 drops of 10 percent sulphuric acid was stirred at about 85° C. for 75 minutes, then heated to boiling for 1 hour, whereby moist solvent distilled off and was replaced by fresh toluene. The reaction mixture was treated with 12 drops of triethylamine and, after cooling, washed three times with 15 ml of water, dried over sodium sulphate, filtered and concentrated. Chromatography of the residue (1.86 g) on 50 g of silica gel with hexane/ethyl acetate (vol. 9:1) and two-fold recrystallization from 8 ml of hexane each time gave 0.65 g of pure 2-fluoro-4-[trans-4-[trans-5-(1E-pentenyl)-1,3-dioxan-2-yl]cyclohexyl]-benzonitrile, m.p. (C-N) 91.2° C., cl.p. (N-I) 192.5° C.

In an analogous manner there can be manufactured:

2-Fluoro-4-[trans-4-[trans-5-vinyl-1,3-dioxan-2-yl]cyclo-hexyl]benzonitrile;

2-fluoro-4-[trans-4-[trans-5-(1E-propenyl)-1,3-dioxan-2-yl]cyclohexyl]benzonitrile, m.p. (C-N) 95.3° C., cl.p. (N-I) 208.5° C.;

2-fluoro-4-[trans-4-[trans-5-(1E-butenyl)-1,3-dioxan-2-yl]cyclohexyl]benzonitrile, m.p. (C-N) 96.9° C., cl.p. (N-I) 198° C.;

2-fluoro-4-[trans-4-[trans-5-(1E-hexenyl)-1,3-dioxan-2-yl]cyclohexyl]benzonitrile;

2-fluoro-4-[trans-4-[trans-5-(1E-heptenyl)-1,3-dioxan-2-yl]cyclohexyl]benzonitrile;

2-fluoro-4-[trans-4-[trans-5-(3-butenyl)-1,3-dioxan-2-yl]cyclohexyl]benzonitrile, m.p. (C-N) 88.6° C., cl.p. (N-I) 152° C.;

2-fluoro-4-[trans-4-[trans-5-(3E-pentenyl)-1,3-dioxan-2-yl]cyclohexyl]benzonitrile;

2-fluoro-4-[trans-4-[trans-5-(3E-hexenyl)-1,3-dioxan-2-yl]cyclohexyl]benzonitrile;

2-fluoro-4-[trans-4-[trans-5-(3E-heptenyl)-1,3-dioxan-2-yl]cyclohexyl]benzonitrile;

2-fluoro-4-[trans-4-[trans-5-(4-pentenyl)-1,3-dioxan-2-yl]cyclohexyl]benzonitrile, m.p. (C-N) 54.6° C., cl.p. (N-I) 128° C.;

2-fluoro-4-[trans-4-[trans-5-(4Z-hexenyl )-1,3-dioxan-2-yl]cyclohexyl]benzonitrile;

2-fluoro-4-[trans-4-[trans-5-(4Z-heptenyl)-1,3-dioxan-2-yl]cyclohexyl]benzonitrile;

2-fluoro-4-[trans-4-[trans-5-(5-hexenyl)-1,3-dioxan-2-yl]cyclohexyl]benzonitrile;

2-fluoro-4-[trans-4-[trans-5-(5-heptenyl)-1,3-dioxan-2-yl]cyclohexyl]benzonitrile.

EXAMPLE 2

In order to investigate the properties of the compounds of formula I in mixtures, binary mixtures (BM) with 4-(trans-4-pentylcyclohexyl)benzonitrile were prepared. The threshold potential and the response times were measured at 22° C. in a TN cell (low bias tilt) having a plate separation of 8 μm; the 2.5-fold value of the threshold potential ($V_{10}$) was chosen as the operating voltage. The corresponding data for 4-(trans-4-pentylcyclohexyl) benzonitrile are: cl.p. (N-I)=54.6° C., $V_{10}$=1.62 V, $t_{on}$=22 ms, $t_{off}$=42 ms, $\Delta n$=0.120.

BM-1

90 wt. % of 4-(trans-4-pentylcyclohexyl)benzonitrile 10 wt. % of 2-fluoro-4-[trans-4-[trans-5-(1E-propenyl)-1,3-dioxan-2-yl]cyclohexyl]benzonitrile cl.p. (N-I) 61.3° C., $V_{10}=1.56$ V, $t_{on}=28$ ms, $t_{off}=50$ ms, $\Delta n=0.125$.

BM-2

80 wt. % of 4-(trans-4-pentylcyclohexyl)benzonitrile 20 wt. % of 2-fluoro-4-[trans-4-[trans-5-(1E-propenyl)-1,3-dioxan-2-yl]cyclohexyl]benzonitrile cl.p. (N-I) 69.2° C., $V_{10}=1.50$ V, $t_{on}=33$ ms, $t_{off}=60$ ms, $\Delta n=0.129$.

We claim:

1. A compound of the formula

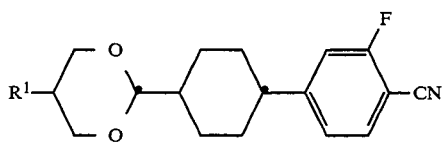

wherein $R^1$ represents vinyl or straight-chain alkenyl with 3 to 7 carbon atoms.

2. A compound in accordance with claim 1, wherein $R^1$ represents vinyl or straight-chain alkenyl with 3 to 5 carbon atoms.

3. A compound in accordance with claim 2, wherein $R^1$ represents vinyl or straight-chain 1E-alkenyl or 3E-alkenyl with 3 to 5 carbon atoms.

4. A liquid crystalline mixture with at least two components, wherein at least, one component is a compound of the formula

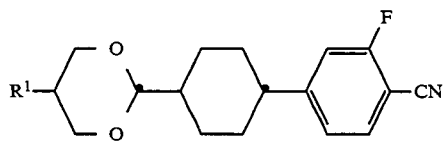

wherein $R^1$ represents vinyl or straight-chain alkenyl with 3 to 7 carbon atoms.

5. A liquid crystalline mixture in accordance with claim 4, wherein the content of compounds of formula I is 1–50 wt. %.

6. A process for the manufacture of compounds of the formula

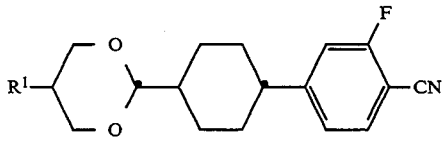

wherein $R^1$ represents vinyl or straight-chain alkenyl with 3 to 7 carbon atoms, which process comprises reacting an enol ether of the formula

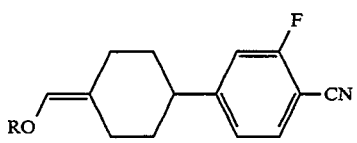

wherein R signifies lower alkyl, with a 1,3-diol of the formula

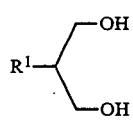

wherein $R^1$ has the above significance, in an inert organic solvent while heating in the presence of water and an acidic catalyst.

7. A liquid crystalline mixture in accordance with claim 5, wherein the content of compounds of formula I is 3–20 wt. %.

* * * * *

UNITED STATES PATENT AND TRADEMARK OFFICE
CERTIFICATE OF CORRECTION

PATENT NO. : 5,447,658

DATED : September 5, 1995

INVENTOR(S) : Richard Buchecker, Teodor Lukac, Martin Schadt, Haruyoshi Takatsu, Alois Villiger It is certified that error appears in the above-identified patent and that said Letters Patent is hereby corrected as shown below:

On the title page:

The following PCT information should be inserted under item:

"[22] Filed:   Jun. 17, 1994"

--- [86]   PCT No.         PCT/EP 92/02112      9/15/92

Switzerland     2899/91              10/01/91

Switzerland     2339/92              07/23/92---.

Foreign Application Priority Data should read

---Oct. 1, 1991 [CH]    Switzerland .......2899/91

Jul. 23, 1992 [CH]   Switzerland........2339/92---.

Signed and Sealed this

Twenty-eighth Day of November 1995

Attest:

BRUCE LEHMAN

*Attesting Officer*    *Commissioner of Patents and Trademarks*